United States Patent
Le Bihan et al.

(10) Patent No.: US 6,806,703 B2
(45) Date of Patent: Oct. 19, 2004

(54) METHOD FOR MEASURING A WALL THICKNESS OF A HOLLOW VANE

(75) Inventors: Yann Le Bihan, Cadan (FR); Olivier Lespinet, Corbeil-Essonnes (FR); Alain Mourenko, Saint Ouen l'aumône (FR); Franck Paul Dominique Vital Panizzoli, Fontainebleau (FR); Dominique Marc Bruno Placko, Creteil (FR); Edouardo-Agapito Santander-Rojas, Nice (FR)

(73) Assignees: Snecma Moteurs, Paris (FR); Centre National de la Recherche Scientifique, Paris Cedex (FR)

( * ) Notice: Subject to any disclaimer, the term of this patent is extended or adjusted under 35 U.S.C. 154(b) by 0 days.

(21) Appl. No.: 10/314,250

(22) Filed: Dec. 9, 2002

(65) Prior Publication Data

US 2003/0184287 A1 Oct. 2, 2003

Related U.S. Application Data

(63) Continuation of application No. 10/069,727, filed as application No. PCT/FR01/02057 on Jun. 28, 2001, now abandoned.

(30) Foreign Application Priority Data

Jun. 29, 2000 (FR) .............................. 00 08368

(51) Int. Cl.[7] .................................................. G01B 7/06
(52) U.S. Cl. ...................................... 324/229; 324/239
(58) Field of Search .............................. 324/242, 243, 324/219, 220, 228, 229–231, 223, 234, 238, 239, 240

(56) References Cited

U.S. PATENT DOCUMENTS 5,140,264 A * 8/1992 Metala et al. ............... 324/219

FOREIGN PATENT DOCUMENTS

EP          0 819 944      * 1/1998
RU          2199089        * 2/2003

* cited by examiner

Primary Examiner—Jay Patidar
(74) Attorney, Agent, or Firm—Olbon, Spivak, McClelland, Maier & Neustadt, P.C.

(57) ABSTRACT

An eddy current detector includes two poles aligned in the direction of extension of partitions located behind a wall, wherein the thickness must be measured, but which interfere with the measurements. The influence of the partitions is decreased by the core of the detector including two poles aligned in the direction of the extension of the partitions and by using a logical system to correct the results obtained according to preliminary results obtained on a reference surface.

9 Claims, 5 Drawing Sheets

METHOD FOR MEASURING A WALL THICKNESS OF A HOLLOW VANE

CROSS REFERENCE TO RELATED APPLICATION

Figure 1:
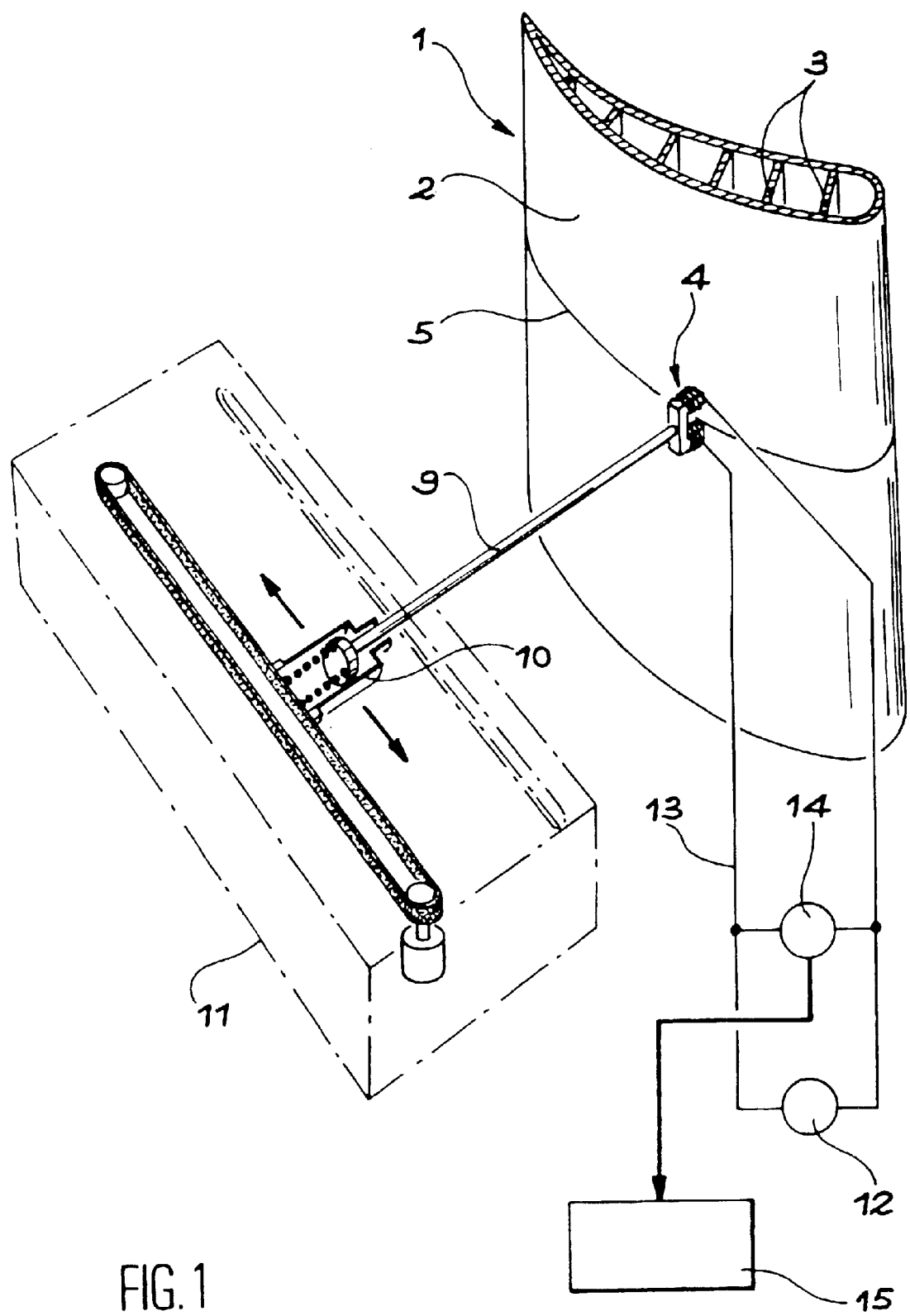

This is a Continuation Application of application Ser. No. 10/069,727, filed on Feb. 28, 2002 now abandoned, which is a national stage of PCT Application No. PCT/FR01/02057, filed on Jun. 28, 2001. This application is based upon and claims the benefit of priority from the prior French Patent Application No. 00-08368, filed on Jun. 29, 2000 the entire contents of which are incorporated herein by reference.

This invention relates to measuring the thickness of a wall of a hollow vane.

One of the characteristics of these parts is that they are normally equipped with internal partitions covered by the wall, in order to stiffen the vane or divide the internal volume into compartments. These partitions interfere with measurements since their contributions to the measurement signal are superimposed with those of the wall and therefore they tend to be confused with additional thicknesses. Several non-destructive methods already exist that are liable to perform thickness measurements, but some, such as X-ray tomography where a detector network takes successive views around the object to be examined, are too complicated to use, while others, such as infrared measurements, are insufficiently accurate. Finally, ultrasound measurements are not suitable for all materials, particularly those which are anisotropic.

A particularly non-destructive thickness measurement method free of these shortcomings has been developed to give accurate and reliable indications on the thickness of a wall in spite of the presence of partitions behind said wall, at inaccurately known positions and which interfere with the thickness measurements.

The method is based on the use of a specific eddy current detector, which is designed and used such that the contribution of the partitions to the signal detected is minimised, and processing means are proposed to eliminate the influence of the partitions on the measurement substantially. Several specific embodiments are possible, which are more or less refined and give accurate results accordingly.

In its most general form, the invention relates to a method to measure the thickness of a hollow vane wall liable to cover partitions, characterised in that it consists of applying two poles of a magnetic code of an eddy current detector on the wall in parallel alignment with the partitions, the poles 8 being equipped with coils 7 connected to each other in series, moving the detector on the wall perpendicular to the partitions, recording a signal produced by the detector and deducing the thickness of the wall according to preliminary calibrations.

The document U.S. Pat. No. 4,005,359 A discloses an eddy current probe applied to estimate the thickness of a paint or enamel coating on a conductive substrate, it is composed of two windings arranged as a transformer, i.e. associated by electromagnetic induction but not connected electrically.

The document U.S. Pat. No. 5,172,059 A shows that a coil inducing eddy currents in a substrate under it is sensitive to variations in the thickness of said substrate.

Figure 2:
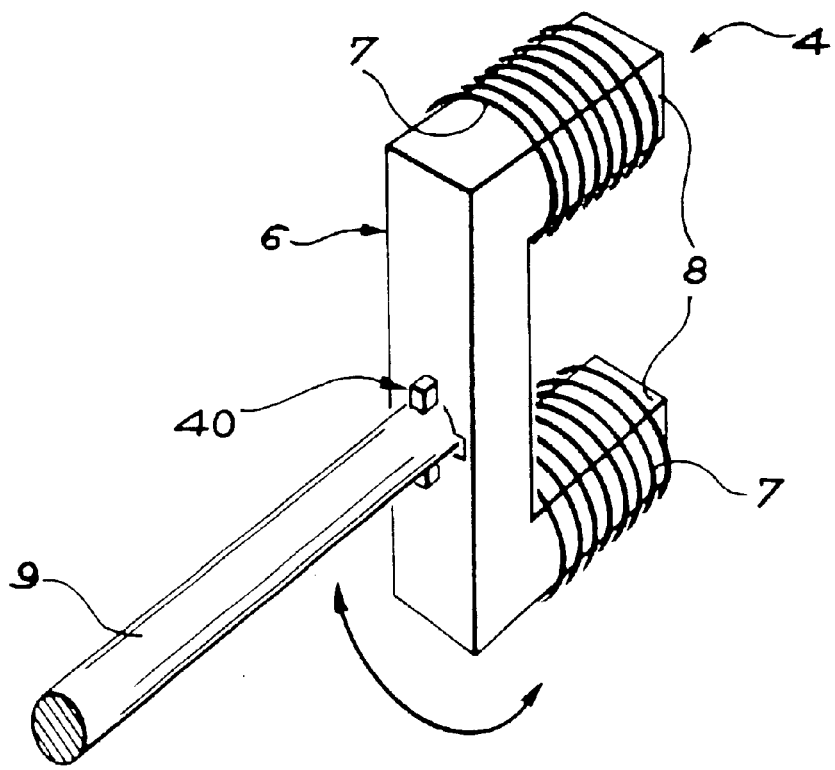
Figure 3:
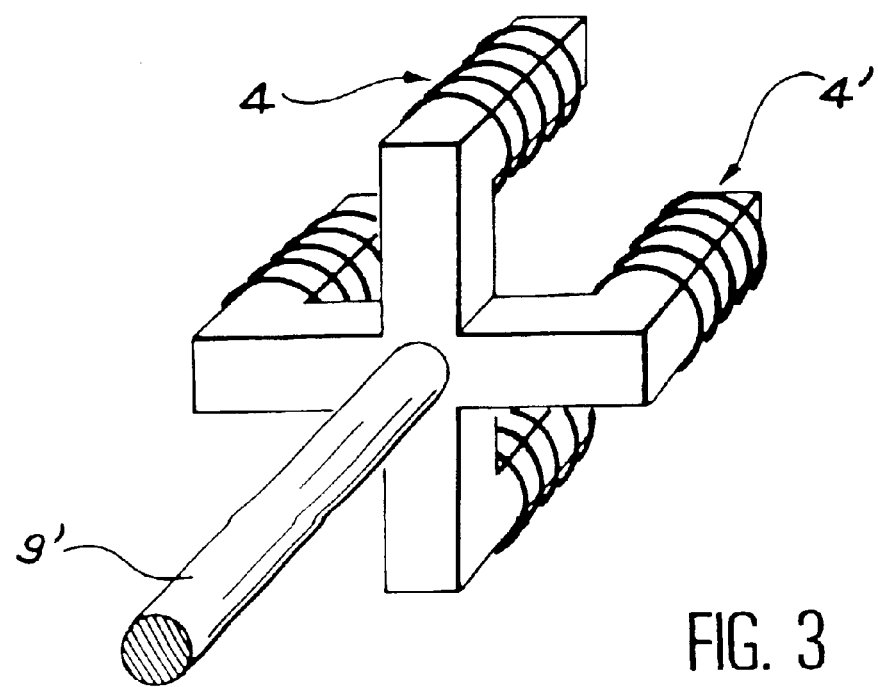
Figure 4:
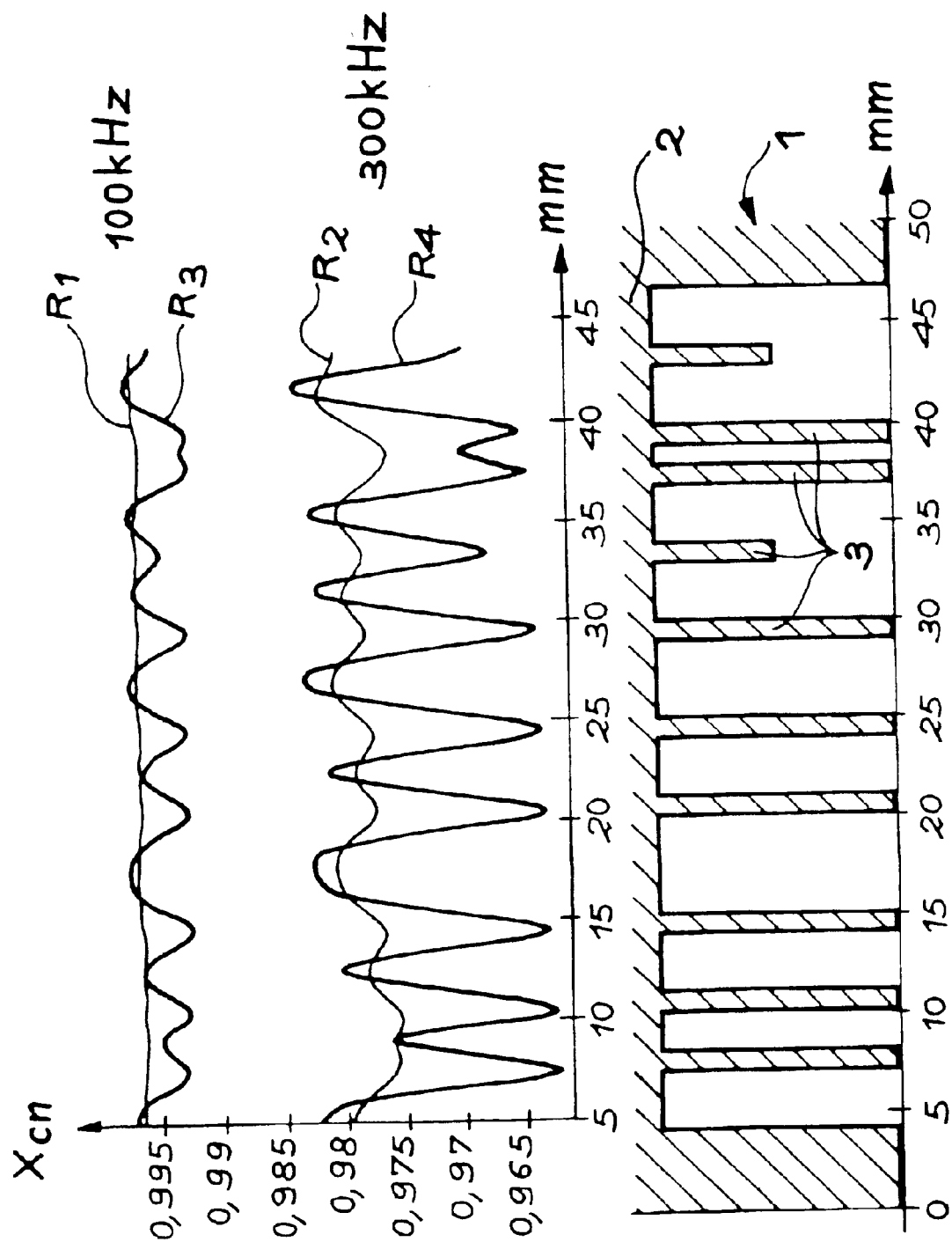
Figure 5:
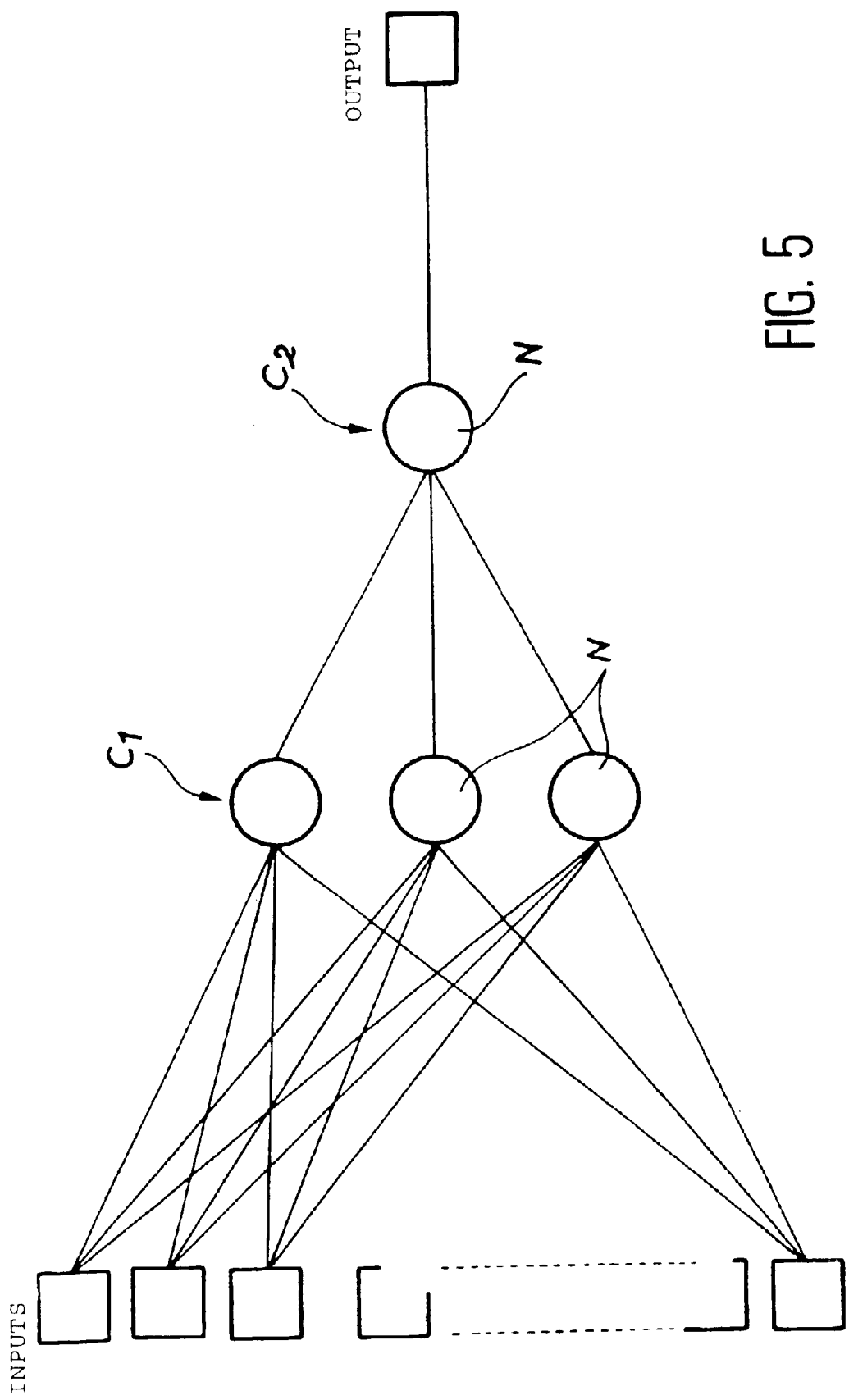
Figure 6:
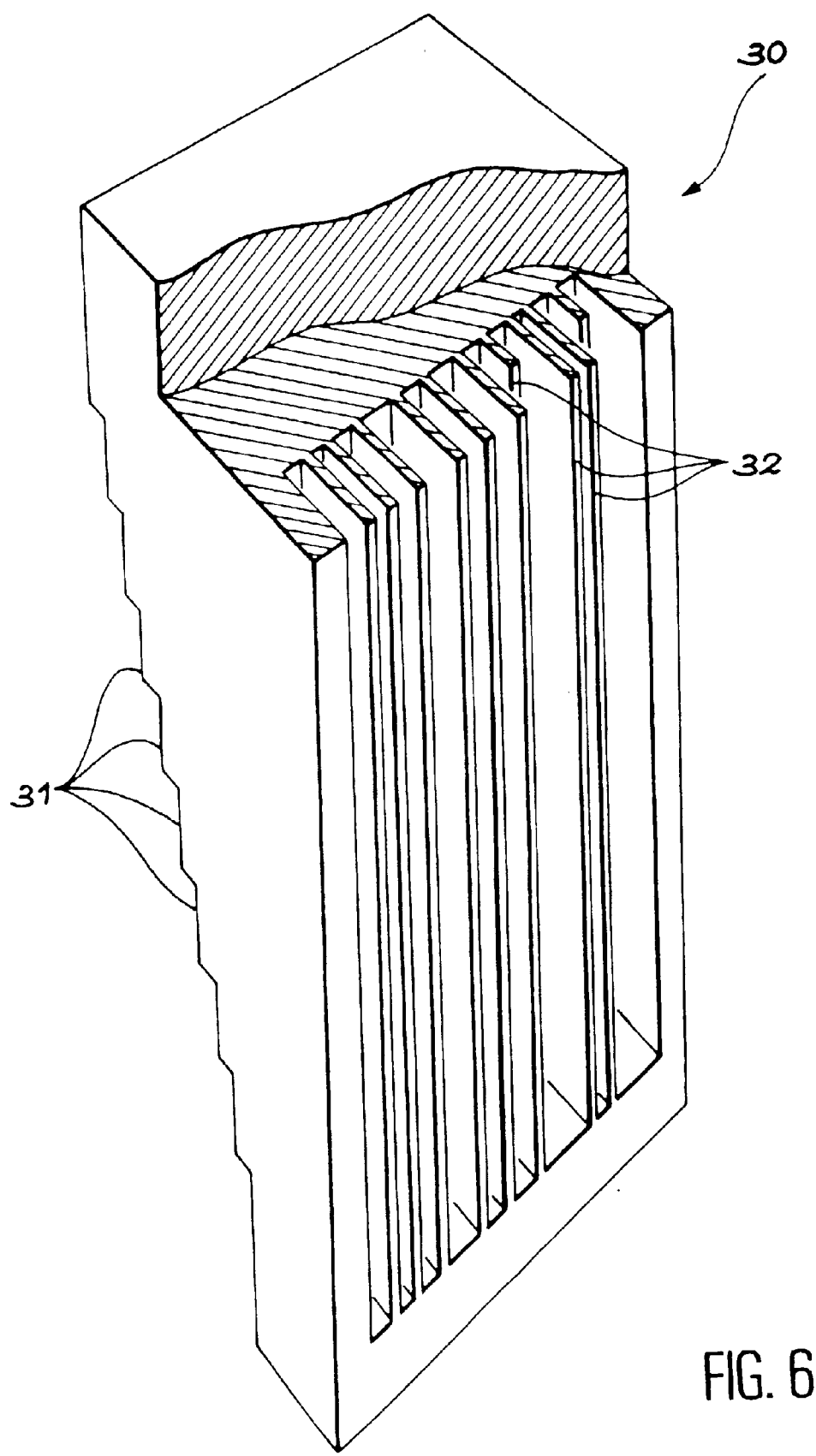

The invention will be described in detail with reference to the following figures, which will show its characteristics, aspects and advantages more clearly, in illustrative embodiments:

FIG. 1 is an overall view of the method;
FIG. 2 illustrates an enlarged view of the detector;
FIG. 3 is a representation of a composite detector;
FIG. 4 is an example of signals obtained;
FIG. 5 illustrates a network of artificial neurones;
and FIG. 6 is a view of a calibration block.

FIG. 1 partially represents a hollow vane 1 wherein the profile is formed by an outer wall 2 stiffened by partitions 3 of different and inaccurately known widths, depths and distances. A sensor 4 is moved along a generatrix 5 of the vane 1. It comprises an arched magnetic core 6, on which an electromagnetic winding is formed, in this case composed of two coils 7 connected to each other in series and placed on the arms 8 of the arch 6. The detector 4 is at the end of a support arm 9 pushed back by a spring 10 such that the ends of the arms 8 touch the wall 2; a motorised device 11 is used to move the arm 9 and the detector 4 along the generatrix 5. An AC generator 12 is placed on an electric circuit 13 to which the coils 7 are connected in series, and a voltmeter 14 is used to record the voltage produced at the terminals of the coils 7 and transmit it to processing means 15 which represent an important part of the invention. The signal measured by the voltmeter 14 particularly depends on the eddy currents produced by the electromagnetic induction of the coils 7 on the portion neighbouring the vane 1, and which depends on, in addition to the thickness of the wall 11, the presence or absence of a partition 3 in front of the detection 4 or in its vicinity. However, it was discovered that, if the poles of the core 6, located at the end of the arms 8, were aligned in the direction of the partitions 3, as shown, the influence of the partitions 3 was much less marked on the probe present, i.e. the signal only varied to a low degree when the detector 4 passed in front of one of the partitions 3. FIG. 4 gives the course of the curve obtained (R1 for an excitation frequency of 100 kHz and R2 for 300 kHz) for a vane profile 1 shown opposite.

If the voltage measured by the voltmeter 14 is $V_B$ and the intensity of the current passing through the coils 7 is I, it is possible to state $$Z_0 = \frac{V_0}{I_0} = R_0 + jX_0$$

where $Z_0$ is the impedance, $R_0$ the resistance and $X_0$ the reactance of the circuit in the off-load state (when the vane 1 is absent), and $$Z_c = \frac{V_c}{I_c} = R_c + jX_c$$

when the detector 4 is applied on the vane 1; j is the imaginary constant ($j^2 = -1$). The processing means can process the measurements particularly by recording the course of the standardised reactance $$X_{cm} = \frac{X_c}{X_0},$$

which is proposed here, or possibly the standardised resistance $$\frac{R_c - R_0}{X_0}.$$

It can be seen that for relatively low induction frequencies, the influence of the partitions 3 becomes almost imperceptible, so much so that it is even possible to envisage ignoring their existence completely and deduce the thickness of the wall 2 directly according to the signal detected, after a preliminary calibration conducted on a series of smooth walls of different thicknesses.

However, it is preferential to use more complex processing operations to deduce the thickness of the walls 2 from the signal obtained, and the processing means 15 where these operations are carried out merits a more detailed description. It contains a network of artificial neurones liable to take the arrangement shown in FIG. 5. In practice, an artificial neurone N is a basic processor which receives a certain number of inputs e with which weights W are associated, and supplies an output s which depends on the weighted inputs and bias b, according to the formula s=F (We+b) where F is an activation function determined by the programming of the neurone N. The input data circulates in the network, being modified at each neurone that they pass through. The neurones may be distributed in successive layers and linked with all the neurones of the previous layer and the next layer. In this case, it was observed that a two-layer network, comprising one output network $C_2$ with a single neurone supplying the desired output (thickness) and a bottom or hidden layer $C_1$ composed of some neurones (two, three or four in practice) fed with the values obtained from the signal ($R_1$ or $R_2$ for example) was sufficient. In addition, the functions carried out by the neurones are the identity (F(W.e+b)=W.e+b) in the layer $C_1$ and the hyperbolic tangent (F(W.e+b)=tanh(W.e+b)) in the layer $C_2$. The neurone network undergoes preliminary training which subsequently enables it to express the descriptive parameters of a new situation, resembling the training situation, according to the signals it receives. It is proposed here to perform a calibration using a plane block 30 (FIG. 6) formed from parallel bands 31 of increasing thickness and provided with ribbing 32, similar to the partitions, behind this plate, at different intervals, possibly of different thicknesses and widths and which intersect with all the bands 31. The detector 4 is moved along these bands 31 in the same way as for the vane 1, so that it supplies a sufficient number of reference signals which are processed to set the neurone network by adjusting the weight and bias of said neurones. Such training of the neurone network may performed automatically by software such that the network outputs the known thickness of each band 31 according to the signals detected along said band.

Although the arrangement of the detector 4 already described is preferred, the measurements may be completed by a similar detector 4', but arranged with poles aligned perpendicular to the partitions 3 (FIG. 3), which gives magnetisation lines perpendicular to said partitions and significant eddy currents in said partitions. It is thus obvious that the influence of the partitions will be much higher on the measurements than with the detector 4, which can be checked on the response curves R3 and R4 in FIG. 4. The signals from the detector 4' supplied to the neurone network with those from the detector 4 makes it possible to correct the influence of the partitions and obtain further improved accuracy for the evaluation of the thickness of the wall 2, since the influence of the partitions 3 is detected better by the detector 4'. An equivalent way to make the measurements would consist, instead of taking the two series of measurements simultaneously by detectors 4 and 4' mounted on a fork-ended support arm 9', of using only the detector 4 provided that it is mounted on the support arm 9 with a coupling 40 used for rotation (FIG. 2). The method would be exactly similar only the two categories of signals would be obtained successively.

Another source of interference is caused by the angle of the detector 4 or 4', which remains in the alignment of the support arm 9, on the vane 3 due to its curvature. However, a correction may be easily made since it is possible to check that the angle only has an effect on the proportions of the real and imaginary parts of the signal supplied by the voltmeter 14. More specifically, it is possible to state Xcn=aRcn+b, where a is a coefficient which depends on the angle of the detector 4 on the vane 1. It is then simply necessary to apply the signals received to an additional neurone network so that it outputs the rectified signal, which is that which would have been obtained with a detector 4 or 4' at a straight angle on the wall 2. Training of the additional neurone network is obtained by moving the detector 4 on the bands 31 with different angles, to determine the values of the coefficient a.

It is necessary to point out that other eddy current detectors, such as axisymmetric central coil detectors transmitting electromagnetic lines in all radiating directions, would only give extremely inaccurate results in this application, while an inaccuracy with a standard deviation of 10 $\mu$m for partitions a few millimetres thick may be expected with the invention.

What is claimed is:

1. Method to measure thickness of a hollow vane wall configured to cover partitions, comprising:
    applying two poles of a magnetic core of an eddy current detector on the wall in parallel alignment with the partitions, the poles being equipped with coils connected to each other in series;
    moving the detector on the wall perpendicular to the partitions;
    recording a first signal produced by the detector; and
    deducing the thickness of the wall according to preliminary calibrations and at least the first signal.

2. Measurement method according to claim 1, further comprising training of a network of neurons by the preliminary calibrations, and wherein the thickness of the wall is deduced by supplying the first signal produced by the detector to an input of the network of neurons.

3. Measurement method according to claim 1, further comprising applying two poles of the magnetic cores of the eddy current detector on the wall in perpendicular alignment to the partitions, moving the detector on the wall perpendicular to the partitions, recording a second signal, produced by the detector, and wherein the thickness of the wall is deduced from the preliminary calibrations and from both the first signal and the second signal.

4. Measurement method according to claim 1, further comprising estimating an angle of the detector on the wall and processing a correction of the thickness deduction utilizing the estimated angle.

5. Method to measure thickness of a hollow vane wall configured to cover partitions, comprising:
    applying poles of a magnetic core of an eddy current detector on the wall in parallel alignment with the partitions, the poles being equipped with coils connected to each other in series;
    moving the detector on the wall perpendicular to the partitions;
    providing a first signal in the coils;
    recording a characteristic of the first signal that depends on the thickness of the wall; and
    deducing the thickness of the wall according to preliminary calibrations made by the detector on reference walls having different known thicknesses and at least the characteristic of the first signal that depends on the thickness of the wall.

6. Measurement method according to claim 5, characterized in that the reference walls each cover partitions separated by different intervals.

7. Measurement method according to claim 5, further comprising training of a network of neurons by the preliminary calibrations, and wherein the thickness of the wall is deduced by supplying the first signal produced by the detector to an input of the network of neurons.

8. Measurement method according to claim 5, further comprising applying two poles of the magnetic cores of the eddy current detector on the wall in perpendicular alignment to the partitions, moving the detector on the wall perpendicular to the partitions, recording a second signal, produced by the detector, and wherein the thickness of the wall is deduced from the preliminary calibrations and from both the first signal and the second signal.

9. Measurement method according to claim 5, further comprising estimating an angle of the detector on the wall and processing a correction of the thickness deduction utilizing the estimated angle.

* * * * *

UNITED STATES PATENT AND TRADEMARK OFFICE
CERTIFICATE OF CORRECTION

PATENT NO. : 6,806,703 B2
DATED : October 19, 2004
INVENTOR(S) : Yann Le Bihan et al.

It is certified that error appears in the above-identified patent and that said Letters Patent is hereby corrected as shown below:

Title page,
Item [75], Inventors, chagne "Yann Le Bihan, Cadan" to -- Yann Le Bihan, Cachan --.

Signed and Sealed this

Twenty-fourth Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,806,703 B2
DATED : October 19, 2004
INVENTOR(S) : Yann Le Bihan et al.

It is certified that error appears in the above-identified patent and that said Letters Patent is hereby corrected as shown below:

<u>Title page,</u>
Item [75], Inventors, change "Yann Le Bihan, Cadan" to -- Yann Le Bihan, Cachan --.

This certificate supersedes Certificate of Correction issued May 24, 2005.

Signed and Sealed this

Sixth Day of September, 2005

JON W. DUDAS
*Director of the United States Patent and Trademark Office*